US012741147B2

(12) United States Patent
Jayakumar et al.

(10) Patent No.: US 12,741,147 B2
(45) Date of Patent: Sep. 22, 2026

(54) CUSTOMIZABLE SIGNAL PROCESSING FOR CLOSED-LOOP NEUROMODULATION THERAPY

(71) Applicant: Boston Scientific Neuromodulation Corporation, Valencia, CA (US)

(72) Inventors: Adarsh Jayakumar, Valencia, CA (US); Andrew James Haddock, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 268 days.

(21) Appl. No.: 18/652,665

(22) Filed: May 1, 2024

(65) Prior Publication Data

US 2024/0382756 A1 Nov. 21, 2024

Related U.S. Application Data

(60) Provisional application No. 63/467,677, filed on May 19, 2023.

(51) Int. Cl.
*A61N 1/36* (2006.01)
*A61N 1/02* (2006.01)

(52) U.S. Cl.
CPC ......... *A61N 1/36125* (2013.01); *A61N 1/025* (2013.01); *A61N 1/36139* (2013.01)

(58) Field of Classification Search
None
See application file for complete search history.

(56) References Cited

U.S. PATENT DOCUMENTS 8,606,362 B2 12/2013 He et al.
8,620,436 B2 12/2013 Parramon et al.
(Continued)

FOREIGN PATENT DOCUMENTS

CN 105792741 A 7/2016
WO WO-2024242843 A1 11/2024

OTHER PUBLICATIONS

"International Application Serial No. PCT/US2024/027212, International Preliminary Report on Patentability mailed Dec. 4, 2025", 8 pgs.
(Continued)

*Primary Examiner* — Michael T. Holtzclaw
(74) *Attorney, Agent, or Firm* — Schwegman Lundberg & Woessner, P.A.

(57) ABSTRACT

Systems and methods for customizing signal processing in a medical device to improve a closed-loop neuromodulation therapy are disclosed. An exemplary electrostimulation system comprises an electrostimulator to provide a neuromodulation therapy, a sensor circuit to sense a physiological signal from a patient, and a controller circuit. The controller circuit selects a signal transformation model from a plurality of candidate frequency- or time and frequency (TF)-based transformation models based at least on a signal property of the sensed physiological signal. The controller circuit processes the physiological signal using the selected signal transformation model, extract signal amplitude and phase information from the processed signal, and generate a feedback control signal to the electrostimulator to adjust the neuromodulation therapy based on the extracted signal features.

20 Claims, 9 Drawing Sheets

(56) References Cited

U.S. PATENT DOCUMENTS

| | | | | |
|---|---|---|---|---|
| 9,259,574 | B2 | 2/2016 | Aghassian et al. | |
| 9,826,916 | B2 | 11/2017 | Tass | |
| 2010/0286747 | A1 | 11/2010 | Sabesan et al. | |
| 2015/0231402 | A1 | 8/2015 | Aghassian | |
| 2015/0360038 | A1 | 12/2015 | Zottola et al. | |
| 2016/0144183 | A1 | 5/2016 | Marnfeldt | |
| 2018/0055373 | A1* | 3/2018 | Kraiter | A61B 5/352 |
| 2018/0071513 | A1 | 3/2018 | Weiss et al. | |
| 2018/0071520 | A1 | 3/2018 | Weerakoon et al. | |
| 2020/0282218 | A1 | 9/2020 | McDonald | |
| 2022/0266027 | A1 | 8/2022 | Zhang et al. | |
| 2022/0387801 | A1 | 12/2022 | Schmidt et al. | |
| 2024/0065550 | A1* | 2/2024 | Connor | A61M 60/546 |

OTHER PUBLICATIONS

"International Application Serial No. PCT/US2024/027212, International Search Report mailed Aug. 22, 2024", 4 pgs.
"International Application Serial No. PCT/US2024/027212, Written Opinion mailed Aug. 22, 2024", 6 pgs.

* cited by examiner 10
12
(Ec)
14
15
16
17
18
20
22
23
24
26a
26b
28

E5:
E4:
30a
30b
PW
IP
+A
-A
F 10
15
15'
16
32
34
36
40
42a
42b
44

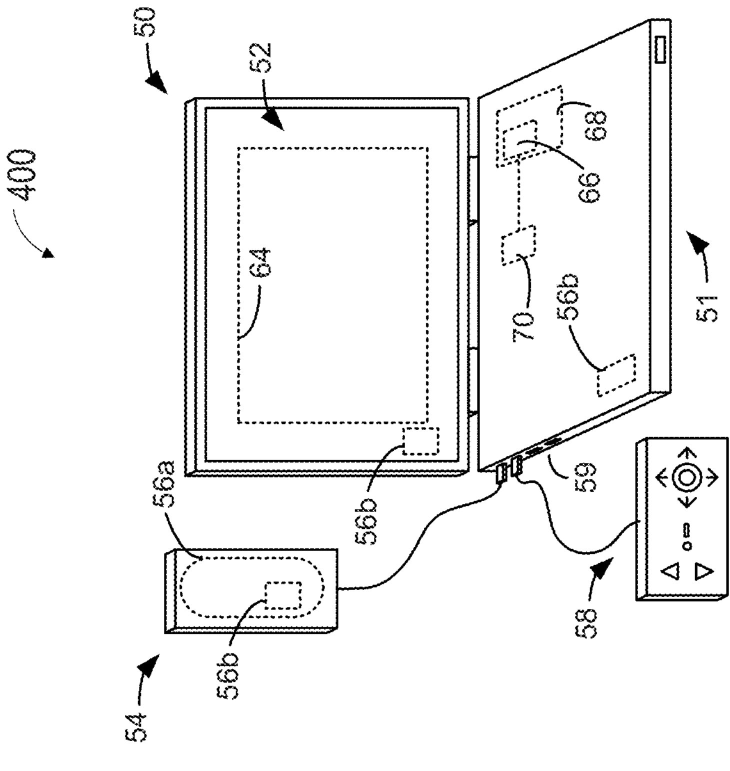
FIG.4
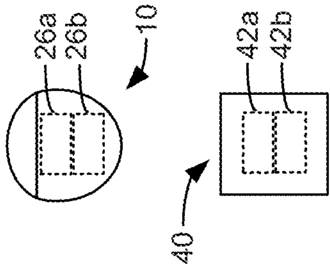
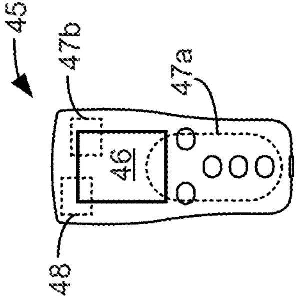

CUSTOMIZABLE SIGNAL PROCESSING FOR CLOSED-LOOP NEUROMODULATION THERAPY

This application claims the benefit of U.S. Provisional Application No. 63/467,677 filed on May 19, 2023, which is hereby incorporated by reference in its entirety.

TECHNICAL FIELD

This document relates generally to medical devices, and more particularly, to systems and devices for providing closed-loop neuromodulation therapy.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS systems have been used as a therapeutic modality for the treatment of chronic pain syndromes. PNS has been used to treat chronic pain syndrome and incontinence, with a number of other applications under investigation. FES systems have been applied to restore some functionality to paralyzed extremities in spinal cord injury patients. DBS can be used to treat a variety of diseases or disorders.

Stimulation systems, such as implantable electrostimulators, have been developed to provide therapy for a variety of treatments. An implantable electrostimulator can include a pulse generator and one or more leads each including a plurality of stimulation electrodes. The stimulation electrodes are in contact with or near target tissue to be stimulated, such as nerves, muscles, or other tissue. The control module generates a control signal to the pulse generator, which generates electrostimulation pulses that are delivered by the electrodes to the target tissue in accordance with an electrode configuration and a set of stimulation parameters.

One example of the neuromodulation therapy is paresthesia-based spinal cord stimulation (SCS) to treat chronic pain. Paresthesia is a sensation such as tingling, prickling, heat, cold, etc. that can accompany SCS therapy. Alternatively, SCS may be delivered with reduced stimulation intensity below a paresthesia threshold to avoid inducing paresthesia, yet still achieve analgesia effect and clinically effective pain relief. Such paresthesia-free SCS, also known as sub-perception SCS, generally uses stimulation pulses at higher frequencies to achieve the paresthesia-free effect, which may consume more power than paresthesia-based SCS.

Closed-loop neuromodulation therapy such as closed-loop SCS can be provided using a feedback control system, where patient response signals are processed and used as feedback to adjust a therapy setting. Proper signal processing of patient response signals is important to maximize therapeutic benefits and avoid or minimize side effects of closed-loop neuromodulation therapies.

SUMMARY

In a closed-loop neuromodulation therapy system, one or more therapy parameters can be adjusted based on feedback information including patient responses to therapy delivered. Examples of such therapy parameters may include stimulation amplitude, frequency, pulse width, waveforms, or electrodes used for delivering stimulation energy, among others. The patient responses can include a physiological signal, such as an electrophysiological signal or a neural activity signal, sensed from the patient in response to the delivered therapy. A digital signal processor (DSP) can filter the physiological signal using one or more filters, transform the signal using a signal transformation model, extract one or more signal features, and assess therapeutic effects and/or side effects with respect to the therapy based on the extracted signal features. In the context of neuromodulation therapy such as SCS or DBS, the signal features may include, among other things, signal amplitude and phase information. For example, in response to electrostimulation at a neural target, electrical signals can be sensed respectively from two or more sense locations (e.g., spinal cord locations or brain regions). The DSP can extract amplitude and phase information from each of the electrical signals, and determine a phase-amplitude coupling or a coherence between the electronical signals based on the amplitude and phase information. The phase-amplitude coupling or the coherence can be used as a feedback to adjust, or to provide a recommendation to adjust, one or more therapy parameters.

Signal transformation such as Hilbert Transform can be used to extract amplitude and phase information from a physiological signal. Based on a special alteration of the Fast Fourier Transform (FFT), the Hilbert Transform can substantially remove the linear-phase component in a frequency response, and produce a minimum-phase response from the spectral analysis of the signal. Conventionally, the Hilbert Transform is implemented as a "static" module in DSP of a neuromodulation device, such that the same Hilbert Transform, when included in the DSP, is invariably applied to a physiological signal regardless of signal type or neuromodulator device collecting the physiological signal. However, the applicability of Hilbert Transform is generally constrained by several factors including an assumption of stationarity and linearity of the signal being analyzed, a reliable and robust estimation of amplitude and phase that is limited to certain narrowband signals, and limitations in stimulation range (i.e., range of values of pulse-width or frequency such that the stimulation artefact can be mitigated for, or limited locations with respect to the stimulation site from which the feedback physiological signals are sensed. Applying Hilbert Transform regardless of inter-signal variabilities in signal frequency characteristics and linearity and stationarity assumptions may introduce more errors to signal amplitude and phase estimation, and reduce the efficacy of closed-loop neuromodulation therapy.

Various signal processing algorithms and tools have been developed and used in various applications, yet relative few are currently used in an implantable neuromodulation device for neural signal processing. The present inventors have recognized the disadvantages of static signal transformation such as Hilbert Transform in a DSP and its impact on a closed-loop neuromodulation therapy, and propose a customizable DSP with flexible selection between different frequency- or time and frequency (TF)-based signal transformation models, and using the selected model to extract signal features such as signal amplitude and phase. According to one embodiment, an electrostimulation system comprises an electrostimulator configured to provide a neuromodulation therapy to a patient, a sensor circuit to sense a physiological signal from the patient, and a controller circuit in operative communication with the electrostimulator. The controller circuit can select a signal transformation model from a plurality of candidate models based at least on a signal property of the sensed physiological signal, process the physiological signal using the selected analysis model, and extract signal amplitude and phase information from the processed physiological signal. Based at least in part on the amplitude and phase information, the controller circuit can generate a control signal to the electrostimulator to adjust the neuromodulation therapy.

A customizable DSP with flexible frequency- or time and frequency (TF)-based signal transformation models as described herein can improve the device-based closed-loop neuromodulation therapy. In accordance with various examples described in this document, the signal transformation models available to the customizable DSP include a Hilbert Transform based model, a Discrete Wavelet transform (DWT) based model, and an Empirical Mode Decomposition (EMD) based model. Each of these models has tradeoffs in terms of computational efficiency, robustness to noise, flexibility across frequency ranges, customizability, and signal property assumptions. The customizable DSP supports frequency- or TF-based analysis for a wide range of physiological signals of different types or having different signal properties. The flexible selection of the signal transformation model can be based on signal of interest, desired power consumption, requirement for more robust estimation of amplitude and phase, or an urgency requirement of the neuromodulation therapy. The flexible signal transformation models can improve the accuracy of amplitude and phase estimates in a physiological signal, and provide better individualized closed-loop neuromodulation therapy to the patient.

Example 1 is a system for providing electrostimulation to a patient, the system comprising: an electrostimulation circuit configured to provide a neuromodulation therapy to the patient; a sensor circuit configured to sense a physiological signal from the patient; and a controller circuit, configured to: select a signal transformation model from a plurality of candidate models based at least on a signal property of the sensed physiological signal; process the physiological signal using the selected signal transformation model; extract amplitude and phase information from the processed physiological signal; and generate a control signal to the electrostimulation circuit to adjust the neuromodulation therapy based at least in part on the extracted amplitude and phase information of the physiological signal.

In Example 2, the subject matter of Example 1 optionally includes the plurality of candidate models that can include one or more frequency-based models or one or more time and frequency-based models.

In Example 3, the subject matter of Example 2 optionally includes the plurality of candidate models that can include a Hilbert transform, a Discrete Wavelet transform, and an Empirical Mode Decomposition.

In Example 4, the subject matter of any one or more of Examples 1-3 optionally includes the signal property of the sensed physiological signal that can include at least one of a signal frequency range, a stationarity or linearity property, or a signal to noise ratio.

In Example 5, the subject matter of any one or more of Examples 1-4 optionally includes the plurality of candidate models each having respective computational complexities, wherein the controller is configured to select the signal transformation model further based on the respective computational complexities for the plurality of candidate models.

In Example 6, the subject matter of any one or more of Examples 1-5 optionally includes the plurality of candidate models each having respective power consumption requirements, wherein the controller is configured to select the signal transformation model further based on the respective power consumption requirements for the plurality of candidate models.

In Example 7, the subject matter of any one or more of Examples 5-6 optionally includes the controller circuit that can be configured to: in response to a selection of a signal transformation model with the computational complexity or power consumption requirement falling below a threshold, control the electrostimulation circuit to deliver a closed-loop neuromodulation therapy; and in response to a selection of a signal transformation model with the computational complexity or power consumption requirement exceeding the threshold, control the electrostimulation circuit to deliver an open-loop neuromodulation therapy.

In Example 8, the subject matter of any one or more of Examples 1-7 optionally includes the controller that can be configured to select the signal transformation model further based on an urgency requirement of the neuromodulation therapy, including to select a first signal transformation model for a first urgency requirement and to select a second signal transformation model for a second urgency requirement lower than the first urgency requirement, wherein the second signal transformation model has a higher computational complexity or power consumption requirement than the first signal transformation model.

In Example 9, the subject matter of Example 8 optionally includes the first signal transformation model that can include a Hilbert transform, and the second signal transformation model includes a Discrete Wavelet transform or an Empirical Mode Decomposition.

In Example 10, the subject matter of any one or more of Examples 1-9 optionally includes the sensed physiological signal includes at least one electrical signal sensed from a brain region in response to the neuromodulation therapy delivered to a brain stimulation site.

In Example 11, the subject matter of Example 10 optionally includes the at least one electrical signal that can include electrical signals sensed respectively from at least two brain regions in response to the neuromodulation therapy delivered to a brain stimulation site, wherein the controller is configured to determine a phase-amplitude coupling or a coherence between the electrical signals using the amplitude and phase information extracted from each of the electrical signals, and to adjust the neuromodulation therapy based at least in part on the determined phase-amplitude coupling or the coherence between the electrical signals.

In Example 12, the subject matter of any one or more of Examples 1-11 optionally includes the controller circuit that can be configured to periodically switch from a default signal transformation model to the selected signal transformation model to process the physiological signal.

In Example 13, the subject matter of Example 12 optionally includes the default signal transformation model that can include a Hilbert transform, and the selected signal transformation model includes a Discrete Wavelet transform or an Empirical Mode Decomposition.

In Example 14, the subject matter of any one or more of Examples 1-13 optionally includes the controller circuit that can be configured to, in response to a trigger event, switch from a default signal transformation model to the selected signal transformation model to process the physiological signal.

In Example 15, the subject matter of any one or more of Examples 1-14 optionally includes: an ambulatory medical device comprising the electrostimulation circuit and a customizable signal processing module for processing the physiological signal; and a programming device in operative communication with the ambulatory medical device, the programming device comprising a user interface to receive a user input to modify the customizable signal processing module of the ambulatory medical device using the selected signal transformation model.

Example 16 is a method of providing neuromodulation therapy to a patient via an electrostimulator, the method comprising: sensing a physiological signal from the patient using a sensor circuit; based at least on a signal property of the sensed physiological signal, selecting a signal transformation model from a plurality of candidate models; processing the physiological signal using the selected signal transformation model; extracting amplitude and phase information from the processed physiological signal; and providing a control signal to the electrostimulator to adjust the neuromodulation therapy based at least in part on the extracted amplitude and phase information of the physiological signal.

In Example 17, the subject matter of Example 16 optionally includes the sensed physiological signal that can include electrical signals sensed respectively from at least two brain regions in response to the neuromodulation therapy delivered to a brain stimulation site, the method further comprising: determining a phase-amplitude coupling or a coherence between the electrical signals using the amplitude and phase information extracted from each of the electrical signals; and adjusting the neuromodulation therapy based at least in part on the determined phase-amplitude coupling or the coherence between the electrical signals.

In Example 18, the subject matter of any one or more of Examples 16-17 optionally includes the plurality of candidate models that can include one or more frequency-based models or one or more time and frequency-based models.

In Example 19, the subject matter of any one or more of Examples 16-18 optionally includes the signal property of the sensed physiological signal that can include at least one of a signal frequency range, a stationarity or linearity property, or a signal to noise ratio.

In Example 20, the subject matter of any one or more of Examples 16-19 optionally includes the plurality of candidate models each having respective computational complexities or power consumption requirements, wherein selecting the signal transformation model is further based on the respective computational complexities or power consumption requirements for the plurality of candidate models.

In Example 21, the subject matter of Example 20 optionally includes generating the control signal to adjust the neuromodulation therapy that can include: delivering a closed-loop neuromodulation therapy if the selected signal transformation model has the computational complexity or power consumption requirement falling below a threshold; and delivering an open-loop neuromodulation therapy if the selected signal transformation model has the computational complexity or power consumption requirement exceeding the threshold.

In Example 22, the subject matter of any one or more of Examples 16-21 optionally includes selecting the signal transformation model is based on an urgency requirement of the neuromodulation therapy, including selecting a first signal transformation model for a first urgency requirement and selecting a second signal transformation model for a second urgency requirement lower than the first urgency requirement, wherein the second signal transformation model has a higher computational complexity or power consumption requirement than the first signal transformation model.

The description that follows will generally focus on the use of the invention within a neuromodulation system, such as a DBS system, a SCS system, a Vagus Nerve Stimulation (VNS) system, or a Sacral Nerve Stimulation (SNS) system, among others. In an example, apparatus and methods for detecting (and maintaining) exceptionally small evoked neural activities as described herein can be used to detect evoked neural activities in closed-loop DBS therapy, or therapies of other regions of the nervous system. The following examples illustrate various aspects of the examples described herein.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 4 illustrates, by way of example and not limitation, various external devices capable of communicating with and programming stimulation in an IPG and ETS.

DETAILED DESCRIPTION

This document describes systems and methods for customizing signal processing functionality in a medical device to improve a closed-loop neuromodulation therapy. An exemplary electrostimulation system comprises an electrostimulator to provide a neuromodulation therapy, a sensor circuit to sense a physiological signal from a patient, and a controller circuit. The controller circuit selects a signal transformation model from a plurality of candidate frequency- or time and frequency (TF)-based transformation models based at least on a signal property of the sensed physiological signal. The controller circuit processes the physiological signal using the selected signal transformation model, extract signal amplitude and phase information from the processed signal, and generate a feedback control signal to the electrostimulator to adjust the neuromodulation therapy based on the extracted signal features.

The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Figures 1, 2, 3:
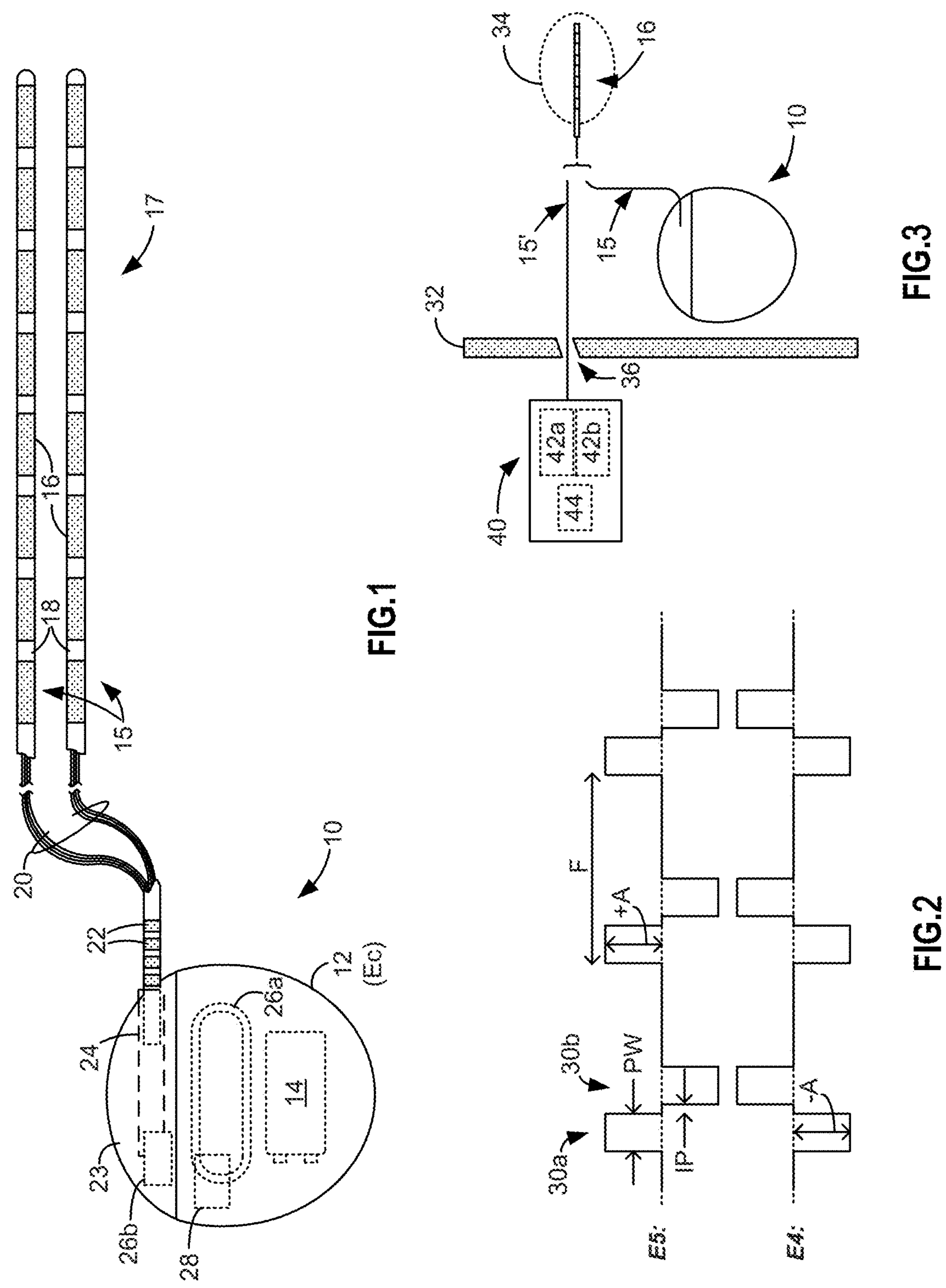
FIG. 1 illustrates, by way of example and not limitation, an Implantable Pulse Generator (IPG) useable for Spinal Cord Stimulation (SCS).
FIG. 2 illustrates, by way of example and not limitation, an example of stimulation pulses producible by an IPG.
FIG. 3 illustrates, by way of example and not limitation, use of an External Trial Stimulator (ETS) useable to provide stimulation before implantation of an IPG.

FIG. 1 illustrates, by way of example and not limitation, an Implantable Pulse Generator (IPG) 10 useable for Spinal Cord Stimulation (SCS). The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

By way of example and not limitation, in the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal contacts 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

The IPG 10 can include an antenna 26*a* allowing it to communicate bi-directionally with a number of external devices, as shown in FIG. 4. The antenna 26*a* as depicted in FIG. 1 is shown as a conductive coil within the case 12, although the coil antenna 26*a* can also appear in the header 23. When antenna 26*a* is configured as a coil, communication with external devices preferably occurs using near-field magnetic induction. IPG may also include a Radiofrequency (RF) antenna 26*b*. In FIG. 1, RF antenna 26*b* is shown within the header 23, but it may also be within the case 12. RF antenna 26*b* may comprise a patch, slot, or wire, and may operate as a monopole or dipole. RF antenna 26*b* preferably communicates using far-field electromagnetic waves. RF antenna 26*b* may operate in accordance with any number of known RF communication standards, such as Bluetooth, Zigbee, WiFi, MICS, and the like.

Stimulation in the IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

FIG. 2 illustrates, by way of example and not limitation, an example of stimulation pulses producible by an IPG, such as the IPG 10. In this example, the electrode E5 has been selected as an anode, and thus provides pulses which source a positive current of amplitude +A to the tissue. Electrode E4 has been selected as a cathode, and thus provides pulses which sink a corresponding negative current of amplitude-A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripolar stimulation, quadripolar stimulation, etc.).

The pulses as shown in FIG. 2 are biphasic, comprising a first phase 30*a*, followed quickly thereafter by a second phase 30*b* of opposite polarity. As is known, use of a biphasic pulse is useful in active charge recovery. For example, each electrodes' current path to the tissue may include a serially connected DC-blocking capacitor, see, e.g., U.S. Patent Application Publication 2016/0144183, which will charge during the first phase 30*a* and discharged (be recovered) during the second phase 30*b*. In the example shown, the first and second phases 30*a* and 30*b* have the same duration and amplitude (although opposite polarities), which ensures the same amount of charge during both phases. In some examples, the second phase 30*b* may be charged balance with the first phase 30*a* if the integral of the amplitude and durations of the two phases are equal in magnitude. The width of each pulse, PW, is defined here as the duration of first pulse phase 30*a*, although pulse width could also refer to the total duration of the first and second pulse phases 30*a* and 30*b* as well. Note that an interphase period during which no stimulation is provided may be provided between the two phases 30*a* and 30*b*.

The IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or in U.S. Pat. Nos. 8,606,362 and 8,620,436. The entirety of such references are incorporated herein by reference.

FIG. 3 illustrates, by way of example and not limitation, use of an External Trial Stimulator (ETS) 40 useable to provide stimulation, and at least a portion of external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42*a*, and/or a far-field RF antenna 42*b*, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 illustrates at least a portion of a neuromodulation system 400. The neuromodulation system 400 comprises the IPG 10 and the ETS 40 as described above with reference to FIGS. 1-3, and various external devices capable of communicating with and programming stimulation in the IPG 10 and the ETS 40, including a patient, hand-held external remote controller (RC) 45, and a clinician programmer (CP) 50. Both the RC 45 and the CP 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

The RC 45 can be as described in U.S. Patent Application Publication 2015/0080982 for example, and may comprise a dedicated controller configured to work with the IPG 10. The RC 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. RC 45 includes a user interface, including means for entering commands (e.g., buttons or icons) and a display 46. The RC 45's user interface enables a patient to adjust stimulation parameters, although it may have limited functionality when compared to the more-powerful CP 50.

In some examples, the RC 45 can have one or more antennas capable of communicating with the IPG 10 and ETS 40. For example, the RC 45 can have a near-field magnetic-induction coil antenna 47*a* capable of wirelessly communicating with the coil antenna 26*a* or 42*a* in the IPG 10 or ETS 40. The RC 45 can also have a far-field RF antenna 47*b* capable of wirelessly communicating with the RF antenna 26*b* or 42*b* in the IPG 10 or ETS 40.

In some examples, the RC 45 can have control circuitry 48 such as a microprocessor, microcomputer, an FPGA, other digital logic structures, an Applicant Specific Integrated Circuit (ASIC), etc., which is capable of executing instructions an electronic device. Control circuitry 48 can for example receive patient adjustments to stimulation parameters, and create a stimulation program to be wirelessly transmitted to the IPG 10 or ETS 40.

The CP 50 can be as described further in U.S. Patent Application Publication 2015/0360038, and is only briefly explained here. The CP 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the CP 50 that are usually specific to its operation as a therapy controller, such as a communication "wand" 54, and a joystick 58, which are coupleable to suitable ports on the computing device 51, such as USB ports 59 for example.

The antenna used in the CP 50 to communicate with the IPG 10 or ETS 40 can depend on the type of antennas included in those devices. If the patient's IPG 10 or ETS 40 includes a coil antenna 26*a* or 42*a*, wand 54 can likewise include a coil antenna 56*a* to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

In an example where the IPG 10 or ETS 40 includes an RF antenna 26*b* or 42*b*, the wand 54, the computing device 51, or both, can likewise include an RF antenna 56*b* to establish communication with the IPG 10 or ETS 40 at larger distances. (Wand 54 may not be necessary in this circumstance). The CP 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. The control circuitry 70 can execute the clinician programmer software 66 to generate a therapy plan and rendering the GUI 64. The therapy plan (also referred to as a stimulation program) may include stimulation parameters chosen through the GUI 64 (e.g., electrode configurations and stimulation dosing parameters). The control circuitry 70 can enable communications via antennas 56*a* or 56*b* to communicate the therapy plan (e.g., stimulation parameters) to the patient's IPG 10. The IPG 10 may deliver electrostimulation in accordance with the therapy plan.

In an example, the therapy plan includes a sub-perception SCS plan comprising stimulation parameters with respective values that can be set by the user via the GUI 64. In some examples, the sub-perception SCS can include a sub-perception therapy program that utilizes a particular stimulation frequency, such as at a level below 100 Hz (or in some instances lower than 10 Hz) and a biphasic-symmetric pulse waveform comprising an active charge phase followed by an active recharge phase. Stimulation pulses in the sub-perception therapy can be defined by stimulation parameters such as stimulation amplitudes, pulse width, frequency, etc. In some examples, sub-perception therapy can be delivered in discreet chunks, or boluses of stimulation pulses. Each bolus comprises stimulation pulses delivered during a first duration, followed by a second stimulation-free duration before a next bolus of stimulation pulses are delivered. A user may use the GUI 64 to program therapy settings, such as electrode selection and configuration, stimulation parameter values including, for example, amplitudes, pulse width, frequency, pulse waveform, active or passive recharge mode for the sub-perception therapy, ON time (the first duration), OFF time (the second duration), and therapy duration, among others. In some examples, the user may use the GUI 64 to define criteria for, and initiate a process of, identifying the patient's usage pattern of stimulation, such as frequency, activation time, duration, and manner of using certain stimulation programs.

Figure 5:
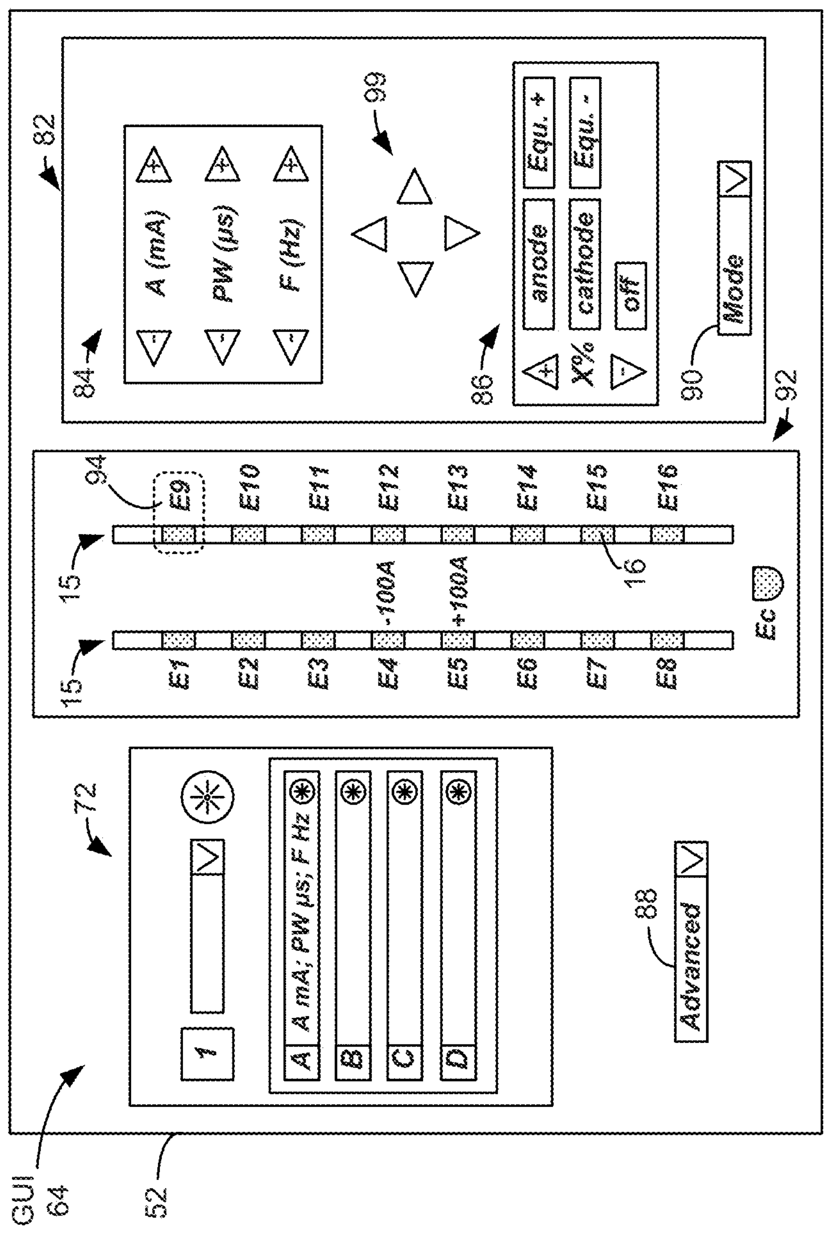
FIG. 5 illustrates, by way of example and not limitation, a Graphical User Interface (GUI) for setting or adjusting stimulation parameters.

FIG. 5 illustrates, by way of example and not limitation, a portion of a GUI (such as one in a clinician programmer) for setting or adjusting stimulation parameters, such as the GUI 64 as shown in FIG. 4. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30*a*. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30*a* and 30*b* (e.g., each having a duration of PW, and with opposite polarities +A and −A). An advanced menu 88 can also be used (among other things) to define the relative durations and amplitudes of the pulse phases 30*a* and 30*b*, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion. While GUI 64 is shown as operating in the CP 50, the user interface of the RC 45 may provide similar functionality.

Figure 6B:
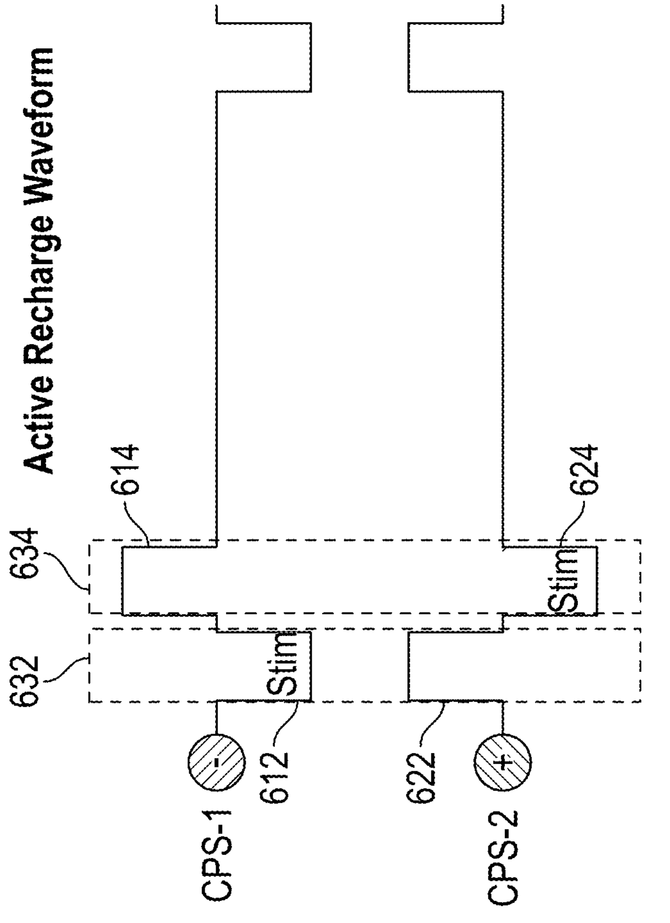
FIGS. 6A-6B illustrate, by way of example and not limitation, schematics of electrode configurations and stimulation waveforms that may be used in fast-acting sub-perception neuromodulation therapy.
Figure 6A:
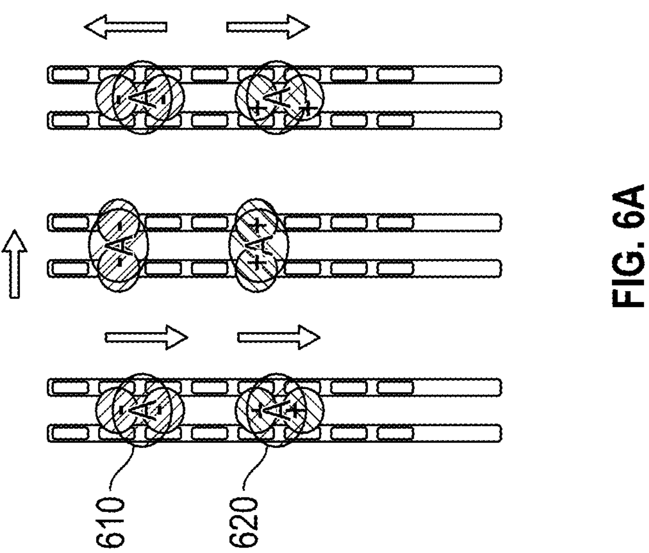

FIGS. 6A-6B illustrate, by way of example and not limitation, schematics of electrode configurations and stimulation waveforms that may be used in a sub-perception neuromodulation therapy. The sub-perception therapy can be programmed using a model-based steering algorithm that enables multiple central points of stimulation (CPS) to be moved rostrocaudally and mediolaterally simultaneously at a programmable step set by a user, as illustrated in FIG. 6A. In the illustrated example, by using symmetric biphasic waveforms, two separate CPSs can be implemented in the stimulation paradigm, including CPS-1 610 representing a virtual cathode, and CPS-2 620 representing a virtual anode. CPS-1 610 and CPS-2 620 can respectively sink or source various percentages of total current across multiple electrodes on the lead (also referred to as "current fractionalization"). For example, current applied to the virtual cathode CPS-1 610 can be fractionalized over a plurality of physical cathodes. Similarly, current applied to the virtual anode CPS-2 620 can be fractionalized over a plurality of physician anodes. The bipolar distance between the CPS-1 610 and CPS-2 620 can be programmed to be within a specified range, such as 10-14 mm. In an example, the bipolar distance is set to approximately 12 mm. The bipolar distance controls the spread of paresthesia during neural target search.

FIG. 6B illustrates biphasic symmetric waveforms of stimulation current for the virtual cathode CPS-1 610 and the virtual anode CPS-2 620. The biphasic symmetric waveform comprises a first charge phase 632, followed by a second active recharge (or charge recovery) phase 634. Current amplitude in each phase remains constant, thus a rectangular waveform. For each of the virtual cathode or the virtual anode, current amplitude of the charge phase 632 has the same magnitude but different sign (representing direction of current flow) than the current amplitude of the recharge phase 634. During the first rectangular phase 632, a negative current 612 (i.e., cathodic current) is injected through negatively configured contacts (physical cathodes corresponding to the virtual cathode CPS-1 610), and positive current 622 (i.e., anodic current) is injected through positively configured return contacts (physical anodes corresponding to the virtual anode CPS-2 620). During the second rectangular phase 634, the polarities of the virtual cathode CPS-1 and the virtual anode CPS-2 are reversed to achieve active charge balance: positive current 614 (i.e., anodic current) is applied to the assigned physical cathodes corresponding to virtual cathode CPS-1 610, and negative current 624 (i.e., cathodic current) is applied to the assigned physical anodes corresponding to virtual anode CPS-2 620.

Stimulation dosing parameters, such as amplitude, frequency (or stimulation rate), pulse width (PW), or waveform pattern of the stimulation waveform are programmable and can be set or adjusted by a user on a GUI. In an example, the frequency of the stimulation pulse (reciprocal of period) can be programmed to a value within a specific range, such as approximately 2-700 Hz. In an example, the stimulation frequency can be programmed to 90 Hz. The pulse width (PW) can be programmed within a range, such as approximately 210±50 micro-seconds (μs). To identify the electrode configuration and fine-tune the location of stimulation, a neural target search can be carried out using the CPS-1 and CPS-2 steered simultaneously in the rostro-caudal and medial-lateral dimensions at a programmable step (resolution) such as in approximately 300 μs increments. The stimulation amplitude can then be lowered to a programmable fraction of the perception threshold. Such a programming for sub-perception therapy allows for a systematic optimization of the stimulating field that provides comprehensive overlap between the area of pain and paresthesia sensation.

Figure 7:
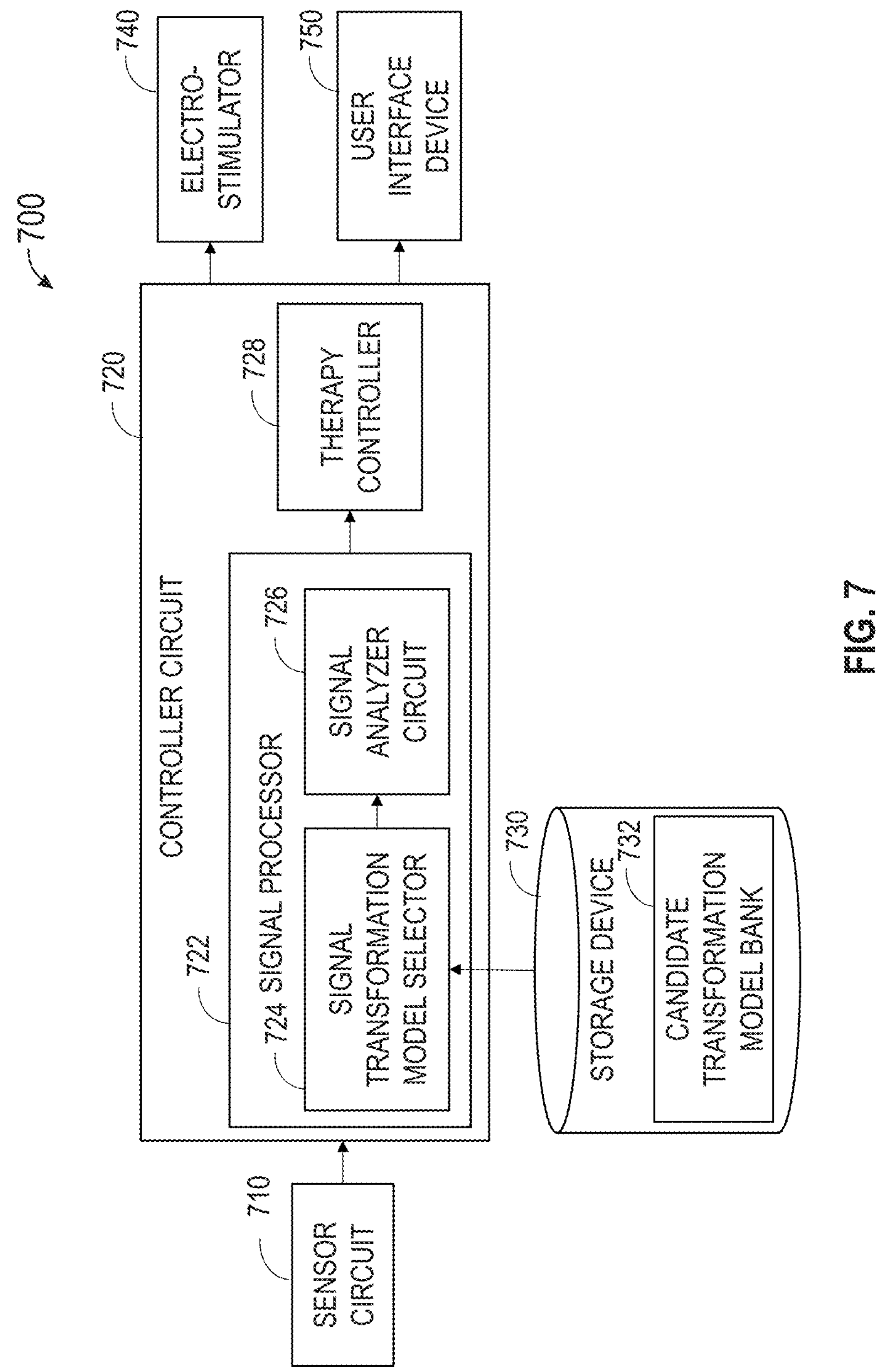
FIG. 7 illustrates, by way of example and not limitation, a neuromodulation system configured to provide or adjust neurostimulation based on a property of a physiological signal received from the patient.

FIG. 7 illustrates, by way of example and not limitation, a neuromodulation system 700 configured to provide or adjust a neuromodulation therapy based on a property of a physiological signal received from the patient. The system 700 can provide a closed-loop neuromodulation therapy to treat or alleviate various neurological or autonomic disorders or other physiological condition. In an example, the system 700 can provide closed-loop spinal cord stimulation (SCS) at a spinal neural target. The SCS can be a part of pain management regimen. In another example, the system 700 can provide closed-loop deep brain stimulation (DBS) at a brain target. The DBS can be used to treat various neurological disorders including, for example, dystonia, epilepsy, essential tremor, or Parkinson's disease. In some examples, the system 700 can titrate neurostimulation to treat or alleviate certain autonomic disorders.

The neuromodulation system 700, which is an embodiment of the neuromodulation system 400, may include one or more of a sensor circuit 710, a controller circuit 720, a storage device 730, an electrostimulator 740, and a user interface device 750. Portions of the neuromodulation system 700 may be implemented in a stimulation device such as the IPG 10 or the ETS 40, or a controller device such as the RC 45 or the CP 50.

The sensor circuit 710 can be coupled to one or more sensors to sense a physiological signal. The one or more sensors may be included in, or external to but communicatively coupled to, the IPG 10 or the ETS 40. In an example, the sensor circuit 710 can be coupled to one or more subcutaneous electrodes on one or more implantable leads, such as the electrodes 16 on one or more electrode leads 15, as illustrated in FIG. 1. The physiological signal can represent patient responses to electrostimulation of a neural target. In an example, the physiological signal sensed by the sensor circuit 710 may include local field potentials (LFPs). The LFPs are transient electrical signals generated in nervous and other tissues (e.g., extracellular space in brain tissue) by the summed and synchronous electrical activity of the individual cells in that tissue. In another example, the sensed physiological signal may include an evoked response induced by electrostimulation pulses produced by the electrostimulator 740 (e.g., included in the IPG 10) and delivered to the neural target via an electrode lead, such as one or more leads 15. The electrostimulation pulses may be generated and delivered to the neural target in accordance with one or more stimulation parameters. Examples of the stimulation parameters can include stimulation waveform dosing parameters such as amplitude (e.g., current amplitude), pulse width, pulse rate or frequency, pulse pattern, pulse waveform, among others. The stimulation parameters may also include electrode configurations that define polarities of the electrodes used for delivering stimulation and fractionalization of current or electrical energy among the electrodes. In some examples, a stimulation pulse train may be delivered in accordance with a pre-defined stimulation program, such as a sub-perception therapy as described above with reference to FIGS. 6A-6B. The evoked response can be sensed from one or more of a dorsal column, a dorsal root, or a peripheral nerve. In some examples, the evoked responses can be somatosensory evoked potential (SSEP) signal recorded by electrodes placed on patient scalp over the sensory area of the brain in response to stimulation of specific nerves in, for example, ankle, wrist, or other external body parts. In an example, a biopotential signal can be sensed by one or more subcutaneous electrodes. The biopotential signal can include an evoked potential or evoked compound action potentials (ECAPs) or evoked resonant neural activities (ERNAs). The evoked responses (corresponding to the stimulation pulses) can include a plurality of inter-pulse segments of a biopotential signal.

In some examples, the physiological signal sensed from the patient may include cardiac, pulmonary, neural, biochemical, or other physiological signals. Some of these signals may reveal characteristic signal properties in response to an onset, intensity, severity, duration, or patterns of pain. Examples of sensor signals can include cardiac signals such as a heart rate signal, a pulse rate signal, a heart rate variability signal, electrocardiogramar intracardiac electrogram, cardiovascular pressure signal, or heart sounds signal, among others. The second signal may additionally or alternatively include a galvanic skin response (GUR) signal, an electrodermal activity (EDA) signal, a skin temperature signal, an electromyogram (EMG) signal, an electroencephalogram (EEG) signal, a magnetoencephelogram (MEG) signal, a hemodynamic signal such as a blood flow signal, a blood pressure signal, a blood perfusion signal, a photoplethysmography (PPG) signal, or a saliva production signal indicating the change of amount of saliva production, among others.

The controller circuit 720, which is an example of the control circuitry 48 of the RC 45 or the control circuitry 70 of the CP 50, can determine an "optimal" or improved therapy setting (as defined by a set of stimulation parameters with respectively optimized values). A therapy setting is deemed "optimal" if the neurostimulation delivered in accordance therewith can produce a desired therapeutic outcome (e.g., adequate pain relief) without producing significant side effects (e.g., discomfort or other symptoms). The controller circuit 720 can include circuit sets comprising one or more other circuits or sub-circuits, such as a signal processor 722 and a therapy controller 728. The signal processor 722 may further include a signal transformation model selector 724 and a signal analyzer circuit 726. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the controller circuit 720 may be implemented as a part of a microprocessor circuit. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the methods or techniques described herein.

Figure 8:
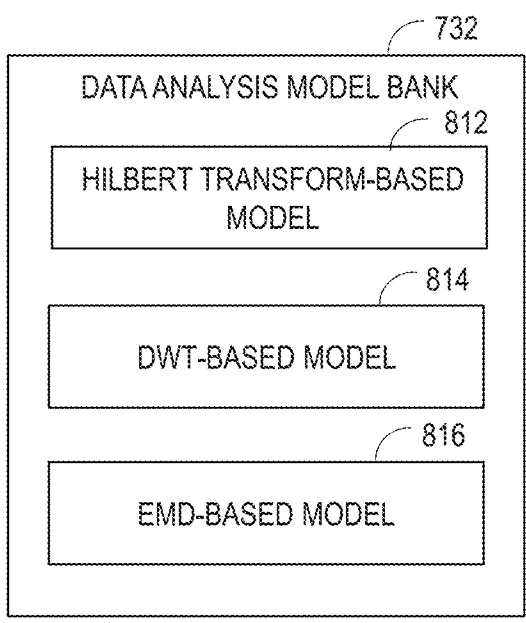
FIG. 8 illustrates examples of frequency- or time and frequency (TF)-based signal transformation models that may be selected for processing a physiological signal.

The signal transformation model selector 724 can select a signal transformation model for the signal analyzer circuit 726 to analyze the received physiological signal. The selection can be made from a candidate signal transformation model bank 732 pre-generated and stored in the storage device 730. Referring to FIG. 8, the candidate signal transformation model bank 732 may store a plurality of frequency- or time and frequency (TF)-based models including a Hilbert transform (HT) based model 812, a Discrete Wavelet transform (DWT) based model 814, and an Empirical Mode Decomposition (EMD) based model 816. The Hilbert transform is a technique used to obtain the minimum-phase response from a spectral analysis. The DWT can extract instantaneous phase and amplitude algorithmically by using a characteristic wavelet (mother wavelet) to approximate the signal of interest. The DWT also allows flexibility to improve performance by customizing the characteristic wavelet for the signal of interest, such as local field potentials in various brain regions or other neural activity signals. The EMD is a data-adaptive multiresolution technique to decompose a signal into physically meaningful components. EMD can be used to analyze non-linear and non-stationary signals by decomposing them into a series of Intrinsic Mode Functions (IMFs) with distinct instantaneous frequencies. The IMFs capture the repeating behavior of the signal at some particular time scale. Like the Fourier transform or the DWT, the EMD reduces a time signal into a set of basis signals; unlike the Fourier or DWT, however, the basis functions are derived from the data itself. The EMD can be used to perform time-frequency analysis while remaining in the time domain. The components are in the same time scale as the original signal, which makes them easier to analyze.

Each of the candidate signal transformation models has tradeoffs in terms of computational efficiency, robustness to noise, flexibility across frequency ranges, customizability, and signal property assumptions. The signal transformation model selector 724 can select the signal transformation model based at least in part on a signal property of the physiological signal received from the sensor circuit 710. By way of example and not limitation, the signal property may include at least one of a signal frequency range, a stationarity or linearity property, or a signal to noise ratio. In some examples, the candidate signal transformation models each have respective distinct computational complexity or power consumption requirement. The signal transformation model selector 724 can select the signal transformation model based at least in part on the computational complexity and power consumption requirement for the plurality of candidate models. For example, for a common input signal, Hilbert transform generally involves less computation and consumes less power than TF-based transforms such as DWT or EMD. Accordingly, if a tighter constraint on computational resources and/or more stringent power saving requirement are imposed on the neuromodulation system, then the Hilbert transform based model 812 may be selected. If the neuromodulation system has sufficient computational resources and a less stringent power saving requirement, then the DWT-based mode 814 or the EMD-based model 816 may be selected. In some examples, the computational complexity or power consumption requirement may be associated with an urgency of neuromodulation therapy. An urgent or time-sensitive therapy requires a minimum delay in therapy delivery, in contrast to a less urgent or time-insensitive therapy that is more tolerant to a delay in therapy. Generally, data analysis using methods with a higher computational complexity may take longer to complete, thereby causing more delay in therapy. The signal transformation model selector 724 can select a signal transformation model based on an urgency requirement of the neuromodulation therapy. For example, if an urgent therapy is desired, then the Hilbert transform based model 812 may be selected; if a less urgent therapy is acceptable, then the DWT-based mode 814 or the EMD-based model 816 may be selected to produce more robust signal amplitude and phase estimates, particularly for non-stationary, non-linear, or wide-band signals.

The signal analyzer circuit 726 may process the physiological signal using the selected signal transformation model. In some examples, the signal analyzer circuit 726 may analyze the physiological signal using a predetermined, default signal transformation model, and periodically switch to the selected signal transformation model to analyze the physiological signal. In an example, the default data basis model can be a Hilbert transform based model, and the selected signal transformation model can be a DWT or EMD based model. The switch from the default signal transformation model to the selected signal transformation model may be manually controlled by the user. Alternatively, the switch can be automatically triggered by a specific event, such as when a signal feature extracted from the physiological signal (e.g., by the signal analyzer circuit 726) fails to satisfy a performance requirement, or when a closed-loop neuromodulation therapy controlled by the therapy controller 728 does not provide adequate or desired therapeutic effects. Other triggered events may include, for example, a user (i.e. clinician) scheduled recording to occur, a fault mode entered such as a fallback or failsafe mode, a diagnostic data collection mode programmed by the device, etc.

The signal analyzer circuit 726 may extract from the processed physiological signal a signal feature that may be used for evaluating neurostimulation efficacy and for closed-loop control of neuromodulation therapy. Depending on the signal transformation model used, the extracted signal feature may include time domain features, frequency domain features, or time-frequency domain features. Examples of the signal features include a signal value range, a signal curve length, or a signal power of an evoked response signal within a time window, such as the epoch-averaged evoked response. The signal amplitude range or value range, also referred to as a peak-to-peak value, can be measured as a difference between a maximum value or a minimum value of the sensed evoked response (or an epoch-averaged evoked response) within the time window. The signal curve length can be measured as accumulated signal value differences of the sensed evoked response (or an epoch-averaged evoked response) over consecutive unit times (e.g., consecutive data sampling intervals) within the time window. The signal power can be measured as an area under the curve (AUC) of the sensed evoked response (or the epoch-averaged evoked response) within the time window.

In some examples, the signal analyzer circuit 726 may extract signal features including amplitude and phase estimated from the processed physiological signal. In some examples, the signal analyzer circuit 726 may determine a phase-amplitude coupling or a coherence between evoked response signals sensed from different sites (e.g., brain regions) in response to stimulation at a neural target. The phase-amplitude coupling relates to a coupling of the phase of slower electrophysiological oscillations (e.g., in a lower frequency band) with the amplitude of faster oscillations (i.e., in a higher frequency band), a phenomenon that facilitates dynamic integration of neural activity in the brain. The frequency bands being analyzed in phase-amplitude coupling may vary depending on the neurological disorders. For example, the phase-amplitude coupling may include a beta-gamma band coupling for Parkinson's disease, or an alpha-gamma band coupling for essential tremor. Algorithms such as Coordinate Rotation Digital Computer (CORDIC) may be implemented in the signal analyzer circuit 726 for rapid calculation of phase-amplitude coupling and/or coherence.

In an example, the signal analyzer circuit 726 can determine an optimal feature from a plurality of candidate signal features based on a predetermined performance criterion. The predetermined performance criterion may include a comparison of discrimination metric value respectively evaluated for the candidate signal features. The discrimination metric measures how well a candidate signal feature can distinguish between different electrostimulation therapy effects, such as therapy effects under different patient conditions or different electrostimulation settings. One example of the discrimination metric is a Fisher's Linear Discriminant (FLD). The FLD is a classification method that projects high-dimensional data onto a line, and performs classification in this one-dimensional space. The projection maximizes the distance between the means of the two classes while minimizing the variance (or standard deviation) within each class. Another example of the discrimination metric is Jensen Shannon Divergence (JSD) metric. The JSD is a measure of the similarity between two probability distributions. The signal analyzer circuit 726 can select the optimal signal feature with the corresponding discrimination metric satisfying a specific selection criterion, such as exceeding a threshold value, or being greater than the discrimination metric values of other candidate signal features.

In some examples, the signal analyzer circuit 726 can determine an optimal signal feature from the received physiological signal using at least one trained machine learning (ML) model. The ML model can be trained using supervised or unsupervised learning algorithms. Supervised learning uses prior knowledge (e.g., examples that correlate inputs to outputs or outcomes) to learn the relationships between the inputs and the outputs. The goal of supervised learning is to learn a function that, given some training data, best approximates the relationship between the training inputs and outputs so that the ML model can implement the same relationships when given inputs to generate the corresponding outputs. Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Examples of DNN include a convolutional neural network (CNN), a recurrent neural network (RNN), a deep belief network (DBN), or a hybrid neural network comprising two or more neural network models of different types of different model configurations, Unsupervised learning is the training of an ML algorithm using information that is neither classified nor labeled, and allowing the algorithm to act on that information without guidance. Unsupervised learning is useful in exploratory analysis because it can automatically identify structure in data. Some common tasks for unsupervised learning include clustering, representation learning, and density estimation. Some examples of commonly used unsupervised learning algorithms are K-means clustering, principal component analysis, and autoencoders. In an example of training a ML model to predict an optimal filter setting (or other signal processing parameter) based on physiological signals acquired under different patient conditions, a training date set can be constructed using patient population data of physiological signals collected under different patient conditions and the filter settings that are demonstrated to provide optimal or desired performance distinguishing therapy effects under different patient conditions. Once trained, the ML model can predict an optimal filter setting (or other signal processing parameter) for the acquired patient condition or contextual information 714.

The therapy controller 728 can generate a control signal to the electrostimulator 740 to adjust the neuromodulation therapy based on the selected signal feature. The electrostimulator 740 can deliver a neuromodulation therapy in accordance with the adjusted therapy setting. Examples of the therapy setting may include, electrode selection and configuration, stimulation parameter values including, for example, amplitudes, pulse width, frequency, pulse waveform, active or passive recharge mode, ON time, OFF time, and therapy duration, among others. In an example, the therapy controller 728 can be implemented as a proportional integral (PI) controller, a proportional-integral-derivative (PID) controller, or other suitable controller that takes measurements of the selected signal feature (e.g., a "range" of epoch-averaged ECAP signal segments) as a feedback on the adjustment of therapy settings.

Figure 9:
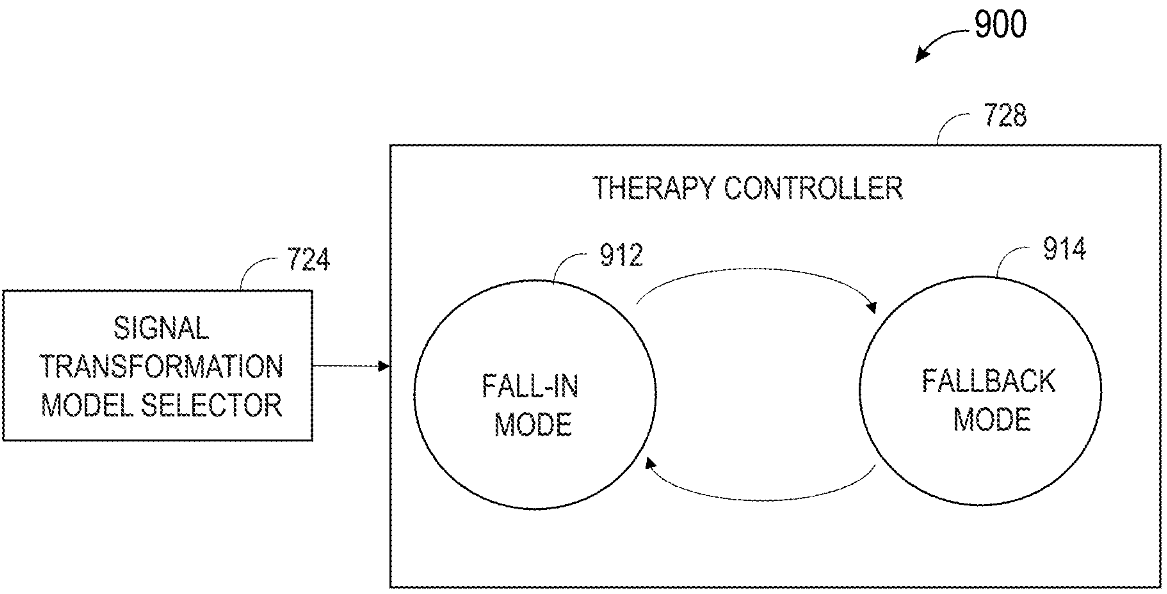
FIG. 9 illustrates a portion of a neuromodulation system that enables switching between a fall-in mode and a fallback mode of neuromodulation therapies.

In some examples, the therapy controller 728 may generate a control signal to command the electrostimulator 740 to operate in either a "fall-in" mode to provide a closed-loop neuromodulation therapy, or alternatively a "fallback" mode to provide an open-loop neuromodulation therapy. Referring to FIG. 9, the diagram 900 illustrate a portion of the system that enables such operation modes and switch therebetween when desired. Under the "fall-in" mode 912, the therapy controller 728 can adjust one or more therapy parameters based on feedback such as evoked responses or physiological signals or a feature extracted therefrom, or patient input about therapeutic effect, side effect, or symptoms. Under the "fallback" mode 914, the therapy controller 728 delivers open-loop neuromodulation therapy in accordance with a predetermined therapy setting regardless of the evoked responses or other feedback information. As stated above, some signal transformation models (e.g., the DWT based model or the EMD based model) have higher computational complexity, require longer data processing time, and cause a longer delay in therapy than other models (e.g., Hilbert transform based model). In certain occasions, it is desirable to use a computationally complex model to process the signal and generate more robust signal features (e.g., signal amplitude and phase estimates, a phase-amplitude coupling, or a coherence between two neural signals), yet without compromising prompt delivery of therapy. To minimize the delay in therapy, the therapy controller 728 may temporarily switch from the "fall-in" mode 912 to the "fallback" mode 914 to provide an open-loop therapy while analyzing the data using a computationally intensive model (e.g., the DWT or EMD based model), and switch back to the "fall-in" mode 912 to provide a closed-loop therapy after the data analysis using the computationally intensive model is completed, at which point a default low computational complexity model (e.g., the Hilbert Transform based model) can be used to analyze patient data. In some examples, if the selected signal transformation model has a computational complexity or power consumption requirement below a threshold, the therapy controller 728 may direct the electrostimulator 740 to deliver a closed-loop therapy. If the selected signal transformation model has a computational complexity or power consumption requirement exceeding the threshold, the therapy controller 728 may direct the electrostimulator 740 to deliver an open-loop therapy.

The electrostimulator 740 can be an implantable module, such as incorporated within the IPG 10. Alternatively, the electrostimulator 740 can be an external stimulation device, such as incorporated with the ETS 40. In some examples, the user can choose to either send a notification (e.g., to the RC 45 or a smartphone with the patient) for a therapy reminder, or to automatically initiate or adjust neuromodulation therapy in accordance with the adjusted therapy setting. If an automatic therapy initiation is selected, the electrostimulator 740 can deliver stimulation in accordance with the adjusted therapy setting.

The user interface device 750 can be a portable (e.g., handheld) device, such as the RC 45 or a smartphone (with executable software application) operable by the patient at his or her home without requiring extra clinic visits or consultation with a device expert. In another example, the user interface device 750 can be a programmer device, such as the CP 50, that allows a physician to remotely review therapy settings and treatment history, consult with the patient to obtain information including pain relief and SCS-related side effects or symptoms, perform remote programming of the electrostimulator 740, or provide other treatment options to the patient. The user interface device 750 can allow a user (e.g., the patient, the physician managing the patient, or a device expert) to view, program, or modify a device setting. For example, the user may use one or more user interface (UI) control elements to provide or adjust values of one or more device parameters, or select from a plurality of pre-defined stimulation programs for future use. Each stimulation program can include a set of stimulation parameters with respective pre-determined values. In some examples, the user interface device 750 can include a display to display textually or graphically information provided by the user via an input unit, and device settings including, for example, feature selection, sensing configurations, signal pre-processing settings, therapy settings, optionally with any intermediate calculations. In an example, the user interface device 750 may present to the user an "optimal" or improved therapy setting, such as determined based on a closed-loop feedback control of electrostimulation based on a selected evoked response signal feature, in accordance with various embodiments discussed in this document.

In some examples, the user can use the interface device 750 to provide feedback on a neuromodulation therapy. The feedback provided by the user via the input unit can include pain data or feedback on pain relief by the existing SCS therapy. The pain data or the feedback on pain relief may include identification of pain sites, distribution of the pain, intensity of pain at various pain sites, or temporal pattern such as persistence of the pain at various pain sites, a pain drawing with pain markings identifying the locations, intensities, patterns of pain, among other information. In some examples, the feedback may include side effects or symptoms arise or persist associated with the SCS, or severity of the symptom or a side effect. The feedback can additionally include, for example, therapeutic effectiveness (e.g., pain relief) of a SCS program, and symptoms or side effects experienced by the patient during the therapy. The feedback provided by the user can include pain data or feedback on pain relief by the existing SCS therapy. The pain data or the feedback on pain relief may include identification of pain sites, distribution of the pain, intensity of pain at various pain sites, or temporal pattern such as persistence of the pain at various pain sites, a pain drawing with pain markings identifying the locations, intensities, patterns of pain, among other information. In some examples, the feedback may include side effects or symptoms arise or persist associated with the SCS, or severity of the symptom or a side effect.

Figure 10:
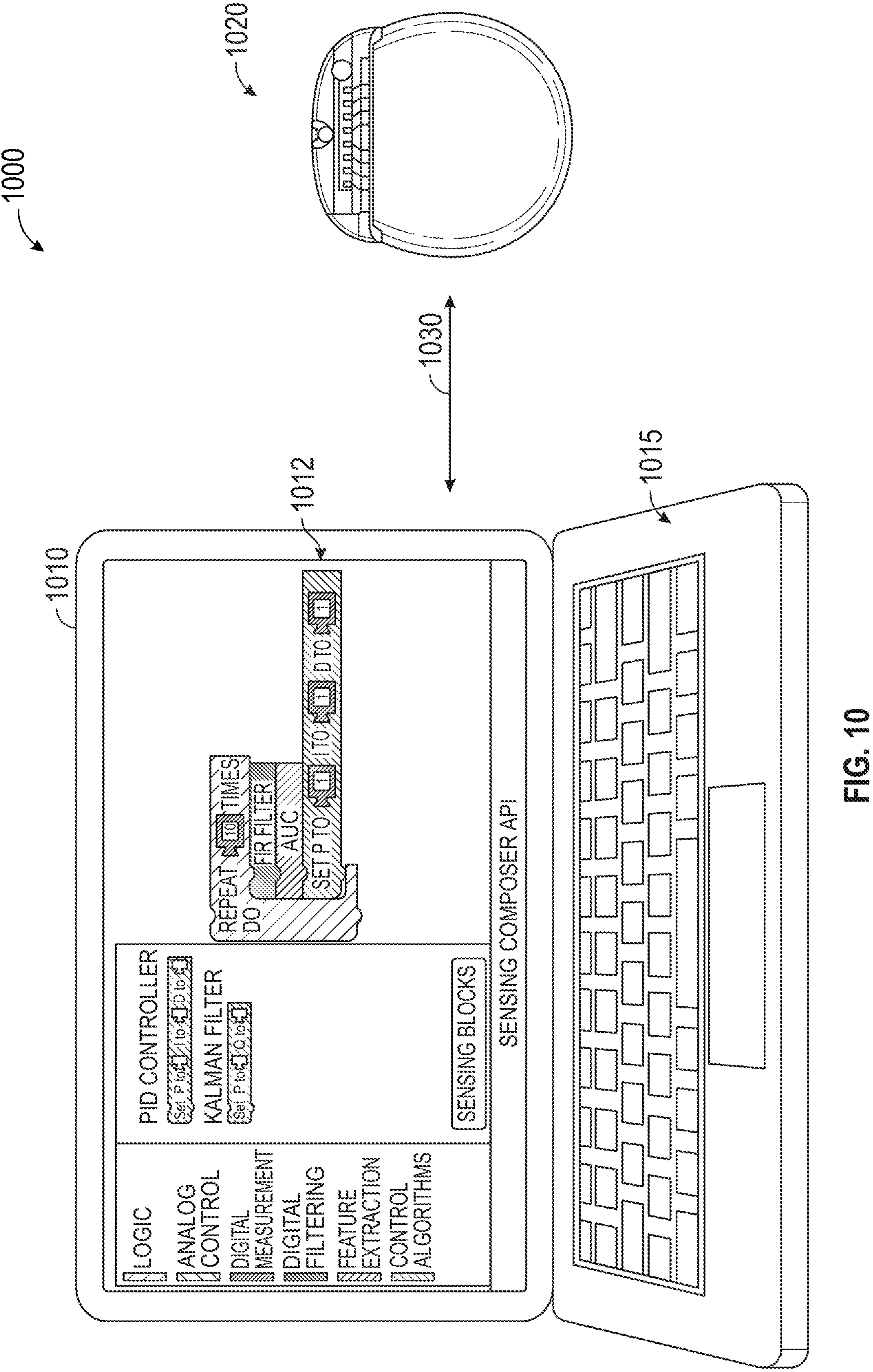
FIG. 10 illustrates, by way of example and not limitation, a portion of a neuromodulation system for customizing signal processing functionalities in an electrostimulator device.

FIG. 10 illustrates, by way of example and not limitation, a portion of a neuromodulation system 1000 for customizing signal processing functionalities in an electrostimulator device. The neuromodulation system 1000 comprises a programmer device 1010 (which can be the CP 50 or the RC 45), and a stimulator device 1020 (which can be the IPG 10 or the ETS 40) in operative communication with the programmer device 1010 via a communication link 1030. The programmer device 1010 includes a graphical user interface comprising a display 1012 and a user input device 1015. Customizable signal processing blocks and corresponding adjustable parameter settings, such as signal transformation models available for selection from the signal transformation model bank 732 and the selected analysis model, can be displayed on the display 1012. A user may use UI control elements to perform various data manipulation and analysis operations including, for example, collecting diagnostic data, configuring digital filters and selecting signal analysis methods, analyzing data, extracting features, and writing signal processing and therapy parameters to IPG 1018. The signal analysis and feature extraction can be conducted locally at the programmer device 1010, and the results displayed on the display 1012. When the results are satisfactory (e.g., the signal feature extracted from the filtered signal satisfies a predetermined performance criterion of distinguishing between different electrostimulation therapy effects), the signal processing parameters (including the selected signal transformation model) can be exported to the stimulator device 1020 via the communication link 1030. In some examples, the programmer device 1010 has a modular design of DSP such that the filter settings, analysis models, along with other DSP functionalities, may be implemented as separate and transferable modules that can be easily transferred to and integrated into the firmware of the stimulator device 1020. The stimulator device 1020 can sense evoked neural response signal, process the signal using the received signal processing parameters (e.g., filter settings, signal transformation models, therapy control algorithms), extract a signal feature such as the optimal feature identified during the signal analysis and feature extraction process by the programmer device 1010. The stimulator device 1020 can evaluate neuromodulation therapy effectiveness or initiate closed-loop control of neuromodulation therapy based on the extracted signal feature.

Figure 11:
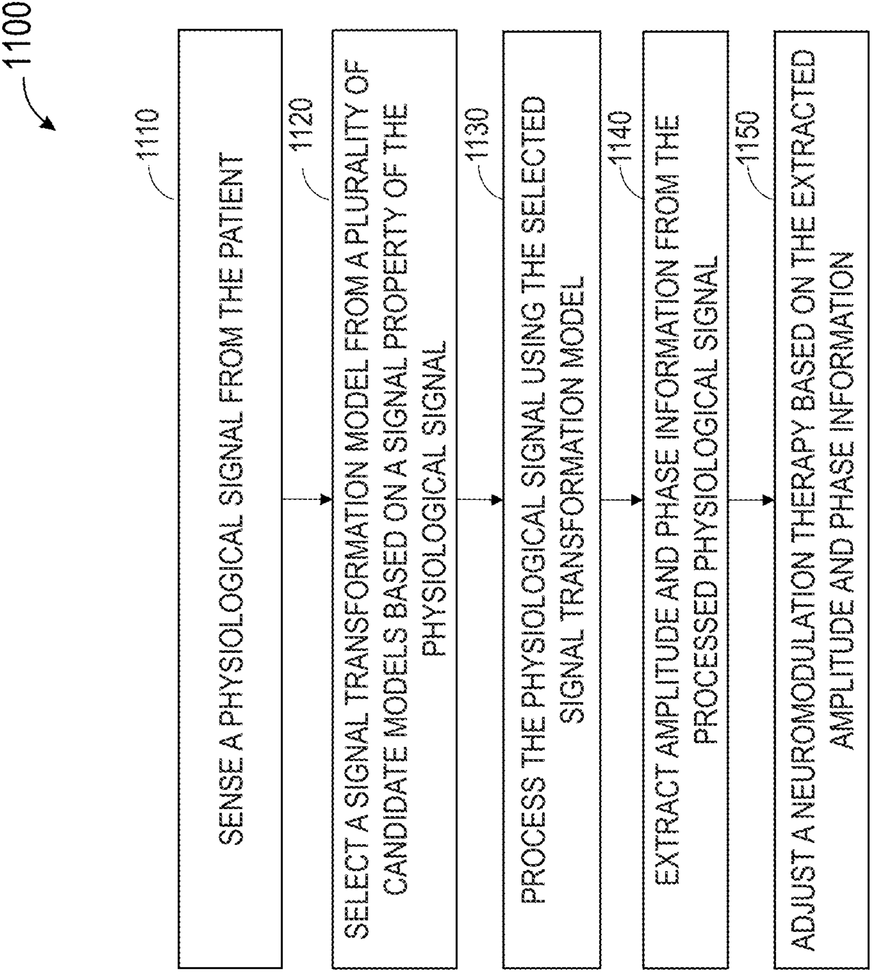
FIG. 11 is a flow chart illustrating, by way of example and not limitation, a method for programming an electrostimulator using a programmer device to provide electrostimulation to a patient.

FIG. 11 is a flow chart illustrating, by way of example and not limitation, a method 1100 for programming an electrostimulator using a programmer device to provide electrostimulation to a patient. The method 1100 may be carried out using a medical system such as the neuromodulation system 400 or the neuromodulation system 700. For example, the method 1100 may be implemented in a programmer device such as the RC 45 or the CP 50, to test and program device parameters to an electrostimulator such as the IPG 10 or the electrostimulator 740. In an example, the method 1100 may be used to program and provide spinal cord stimulation (SCS) at a spinal neural target. The SCS can be a part of pain management regimen. In another example, the method 1100 may be used to provide closed-loop deep brain stimulation (DBS) at a brain target. The DBS can be used to treat various neurological disorders including, for example, dystonia, epilepsy, essential tremor, or Parkinson's disease.

At 1110, a physiological signal can be sensed from the patient, such as using the sensor circuit 710. The physiological signals may be used using one or more subcutaneous electrodes on one or more implantable leads, such as the electrodes 16 on one or more electrode leads 15, as illustrated in FIG. 1. The physiological signal can represent patient responses to electrostimulation of a neural target, such as an evoked response induced by electrostimulation pulses. In some examples, the physiological signal sensed from the patient may include cardiac, pulmonary, neural, biochemical, or other physiological signals.

At 1120, a signal transformation model can be selected from a plurality of candidate models based at least on a signal property of the sensed physiological signal, selecting. The signals transformation model may be used to analyze the physiological signal and extract signal features therefrom. Candidate signal transformation models, which can be pre-generated and stored in a model bank as illustrated in FIG. 7, may include a suite of frequency- or time and frequency (TF)-based models including a Hilbert transform (HT) based model, a Discrete Wavelet transform (DWT) based model, and an Empirical Mode Decomposition (EMD) based model. Each candidate signal transformation model has tradeoffs in terms of computational efficiency, robustness to noise, flexibility across frequency ranges, customizability, and signal property assumptions. Selection of the signal transformation model can be based on signal property of the physiological signal, such as a signal frequency range, a stationarity or linearity property, or a signal to noise ratio. In some examples, the candidate signal transformation models each have respective computational complexities or power consumption requirements. The selection of the signal transformation model can be based on the respective computational complexities or power consumption requirements for the plurality of candidate models. In some examples, the selection of the signal transformation model can be based on an urgency requirement of the neuromodulation therapy. For example, if an urgent therapy is desired, then a Hilbert transform based model may be selected; if a less urgent therapy is acceptable, then a DWT-based mode or a EMD-based model may be selected to produce more robust signal amplitude and phase estimates, particularly for non-stationary, non-linear, or wideband signals.

At 1130, the physiological signal can be processed using the selected signal transformation model. In some examples, a predetermined default signal transformation model can be periodically switched to the selected signal transformation model to analyze the physiological signal. The predetermined default signal transformation model can be a computationally less intensive model, such as a Hilbert transform based model. The selected signal transformation model can be a DWT or EMD based model. The switch from the default signal transformation model to the selected signal transformation model may be manually controlled or automatically triggered by a specific event, such as when a signal feature fails to satisfy a performance requirement, or when a closed-loop neuromodulation therapy does not provide adequate or desired therapeutic outcome.

At 1140, signal features including signal amplitude and phase information may be extracted from the processed physiological signal. Depending on the signal transformation model used, the extracted signal feature may include time domain features, frequency domain features, or time-frequency domain features. Examples of the signal features include a signal value range, a signal curve length, or a signal power of an evoked response signal within a time window, such as the epoch-averaged evoked response. In some examples, the physiological signal sensed from the patient may include electrical signals sensed respectively from at least two brain regions in response to the neuromodulation therapy delivered to a brain stimulation site. Amplitude and phase information can be extracted from each of the brain electrical signals, and a phase-amplitude coupling or a coherence between the electrical signals can be determined using the amplitude and phase information of the electrical signals. The phase-amplitude coupling or the coherence, among other signal features, may be used for evaluating neurostimulation efficacy and for closed-loop control of neuromodulation therapy.

In some examples, an optimal signal feature can be determined from a plurality of candidate signal features based on a predetermined performance criterion. This may include evaluating a discrimination metric for each of multiple candidate signals features extracted from the processed physiological signal. The discrimination metric indicates a performance of the signal feature in distinguishing different stimulation effects under different patient conditions. Example of the discrimination metric include a Fisher's Linear Discriminant (FLD), or a Jensen Shannon Divergence (JSD) metric. An optimal signal feature can be selected as one with corresponding discrimination metric satisfying a specific selection criterion, such as exceeding a threshold value, or being greater than the discrimination metric values of other candidate signal features. In some examples, an optimal signal feature can be determined using a trained machine learning (ML) model.

At 1150, a neuromodulation therapy can be adjusted based on the signal feature determined from step 1140, such as the amplitude and phase information extracted from the filtered physiological signal. A neuromodulation therapy may be delivered in accordance with the adjusted therapy setting, such as using the electrostimulator 740. In some examples, the neuromodulation therapy may be a closed-loop therapy in which case the electrostimulator is said to be operated in an "fall-in" mode, or alternatively an open-loop therapy in which case the electrostimulator is said to be operated in a "fallback" mode. Under the "fall-in" mode, one or more therapy parameters may be adjusted based on feedback such as evoked response or physiological signals or a feature extracted therefrom or patient input such as symptoms, therapeutic or side effects. Under the "fallback" mode, the neuromodulation therapy is delivered according to predetermined stimulation parameter value regardless of the evoked response or other feedback information. In some examples, if the selected signal transformation model has a computational complexity or power consumption requirement falling below a threshold, the electrostimulator can be set to "fall-in" mode and provide a closed-loop therapy. If the selected signal transformation model has a computational complexity or power consumption requirement exceeding the threshold, the electrostimulator can be switched to "fallback" mode and provide an open-loop therapy.

Figure 12:
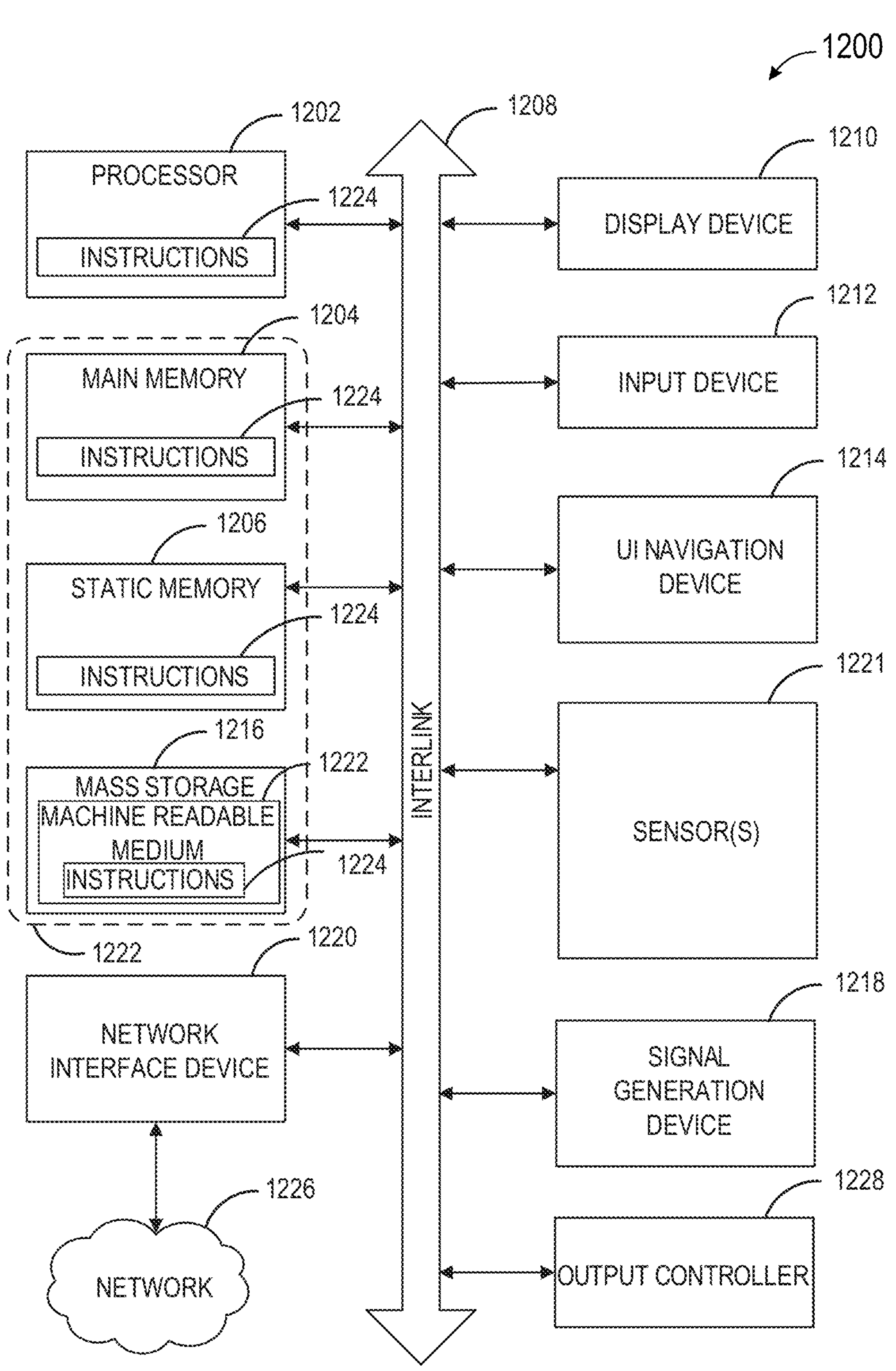
FIG. 12 illustrates generally a block diagram of an example machine upon which any one or more of the techniques (e.g., methodologies) discussed herein may perform.

FIG. 12 illustrates generally a block diagram of an example machine 1200 upon which any one or more of the techniques (e.g., methodologies) discussed herein may perform. Portions of this description may apply to the computing framework of various portions of the neuromodulation device or the external programmer device.

In alternative examples, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), among other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1200 may include a hardware processor 1202 (e.g., a central processing unit (CPU), a graphics processing unit (GPU), a hardware processor core, algorithm specific ASIC, or any combination thereof), a main memory 1204 and a static memory 1206, some or all of which may communicate with each other via an interlink (e.g., bus) 1208. The machine 1200 may further include a display unit 1210 (e.g., a raster display, vector display, holographic display, etc.), an alphanumeric input device 1212 (e.g., a keyboard), and a user interface (UI) navigation device 1214 (e.g., a mouse). In an example, the display unit 1210, input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensors. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1216 may include a machine readable medium 1222 on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1200. In an example, one or any combination of the hardware processor 1202, the main memory 1204, the static memory 1206, or the storage device 1216 may constitute machine readable media. While the machine-readable medium 1222 is illustrated as a single medium, the term "machine readable medium" may include a single medium or multiple media (e.g., a centralized or distributed database, and/or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1224 may further be transmitted or received over a communication network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communication network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software.

Various examples are illustrated in the figures above. One or more features from one or more of these examples may be combined to form other examples.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing electrostimulation to a patient, the system comprising:

an electrostimulation circuit configured to provide a neuromodulation therapy to the patient;

a sensor circuit configured to sense a physiological signal from the patient; and a controller circuit, configured to:

select a signal transformation model from a plurality of candidate models based at least on a signal property of the sensed physiological signal;

process the physiological signal using the selected signal transformation model;

extract amplitude and phase information from the processed physiological signal; and generate a control signal to the electrostimulation circuit to adjust the neuromodulation therapy based at least in part on the extracted amplitude and phase information of the physiological signal.

2. The system of claim 1, wherein the plurality of candidate models include one or more frequency-based models or one or more time and frequency-based models.

3. The system of claim 1, wherein the signal property of the sensed physiological signal includes at least one of a signal frequency range, a stationarity or linearity property, or a signal to noise ratio.

4. The system of claim 1, wherein the plurality of candidate models each have respective computational complexities or power consumption requirements, wherein the controller is configured to select the signal transformation model further based on the respective computational complexities or power consumption requirements for the plurality of candidate models.

5. The system of claim 4, wherein the controller circuit is configured to:

in response to a selection of a signal transformation model with the computational complexity or power consumption requirement falling below a threshold, control the electrostimulation circuit to deliver a closed-loop neuromodulation therapy; and in response to a selection of a signal transformation model with the computational complexity or power consumption requirement exceeding the threshold, control the electrostimulation circuit to deliver an open-loop neuromodulation therapy.

6. The system of claim 1, wherein the controller is configured to select the signal transformation model further based on an urgency requirement of the neuromodulation therapy, including to select a first signal transformation model for a first urgency requirement and to select a second signal transformation model for a second urgency requirement lower than the first urgency requirement, wherein the second signal transformation model has a higher computational complexity or power consumption requirement than the first signal transformation model.

7. The system of claim 6, wherein the first signal transformation model includes a Hilbert transform, and the second signal transformation model includes a Discrete Wavelet transform or an Empirical Mode Decomposition.

8. The system of claim 1, wherein the sensed physiological signal includes at least one electrical signal sensed from a brain region in response to the neuromodulation therapy delivered to a brain stimulation site.

9. The system of claim 8, wherein the at least one electrical signal includes electrical signals sensed respectively from at least two brain regions in response to the neuromodulation therapy delivered to a brain stimulation site, wherein the controller is configured to determine a phase-amplitude coupling or a coherence between the electrical signals using the amplitude and phase information extracted from each of the electrical signals, and to adjust the neuromodulation therapy based at least in part on the determined phase-amplitude coupling or the coherence between the electrical signals.

10. The system of claim 1, wherein the controller circuit is configured to periodically switch from a default signal transformation model to the selected signal transformation model to process the physiological signal.

11. The system of claim 10, wherein the default signal transformation model includes a Hilbert transform, and the selected signal transformation model includes a Discrete Wavelet transform or an Empirical Mode Decomposition.

12. The system of claim 1, wherein the controller circuit is configured to, in response to a trigger event, switch from a default signal transformation model to the selected signal transformation model to process the physiological signal.

13. The system of claim 1, comprising:

an ambulatory medical device comprising the electrostimulation circuit and a customizable signal processing module for processing the physiological signal; and a programming device in operative communication with the ambulatory medical device, the programming device comprising a user interface to receive a user input to modify the customizable signal processing module of the ambulatory medical device using the selected signal transformation model.

14. A method of providing neuromodulation therapy to a patient via an electrostimulator, the method comprising:

sensing a physiological signal from the patient using a sensor circuit;

based at least on a signal property of the sensed physiological signal, selecting a signal transformation model from a plurality of candidate models;

processing the physiological signal using the selected signal transformation model;

extracting amplitude and phase information from the processed physiological signal; and providing a control signal to the electrostimulator to adjust the neuromodulation therapy based at least in part on the extracted amplitude and phase information of the physiological signal.

15. The method of claim 14, wherein the sensed physiological signal includes electrical signals sensed respectively from at least two brain regions in response to the neuromodulation therapy delivered to a brain stimulation site, the method further comprising:

determining a phase-amplitude coupling or a coherence between the electrical signals using the amplitude and phase information extracted from each of the electrical signals; and adjusting the neuromodulation therapy based at least in part on the determined phase-amplitude coupling or the coherence between the electrical signals.

16. The method of claim 14, wherein the plurality of candidate models include one or more frequency-based models or one or more time and frequency-based models.

17. The method of claim 14, wherein the signal property of the sensed physiological signal includes at least one of a signal frequency range, a stationarity or linearity property, or a signal to noise ratio.

18. The method of claim 14, wherein the plurality of candidate models each have respective computational complexities or power consumption requirements, wherein selecting the signal transformation model is further based on the respective computational complexities or power consumption requirements for the plurality of candidate models.

19. The method of claim 18, wherein generating the control signal to adjust the neuromodulation therapy includes:

delivering a closed-loop neuromodulation therapy if the selected signal transformation model has the computational complexity or power consumption requirement falling below a threshold; and delivering an open-loop neuromodulation therapy if the selected signal transformation model has the computational complexity or power consumption requirement exceeding the threshold.

20. The method of claim 14, wherein selecting the signal transformation model is based on an urgency requirement of the neuromodulation therapy, including selecting a first signal transformation model for a first urgency requirement and selecting a second signal transformation model for a second urgency requirement lower than the first urgency requirement, wherein the second signal transformation model has a higher computational complexity or power consumption requirement than the first signal transformation model.

* * * * *